United States Patent [19]

Berg

[11] Patent Number: 5,868,907
[45] Date of Patent: Feb. 9, 1999

[54] SEPARATION OF METHYL ETHYL KETONE FROM ETHANOL BY AZEOTROPIC DISTILLATION

[76] Inventor: Lloyd Berg, 1314 S. 3rd Ave., Bozeman, Mont. 59715

[21] Appl. No.: 106,374

[22] Filed: Jun. 29, 1998

[51] Int. Cl.$^6$ .............................. B01D 3/36; C07C 29/82; C07C 45/84
[52] U.S. Cl. .................................. 203/57; 203/60; 203/70; 568/410; 568/913
[58] Field of Search .................................. 203/57, 60, 68, 203/70; 568/410, 411, 913

[56] References Cited

U.S. PATENT DOCUMENTS

| | | | |
|---|---|---|---|
| 3,764,627 | 10/1973 | Prinz | 568/411 |
| 4,345,976 | 8/1982 | Peter et al. | 203/60 |
| 4,349,415 | 9/1982 | De Filippi et al. | 203/14 |
| 4,395,576 | 7/1983 | Kwantes et al. | 568/913 |
| 4,447,643 | 5/1984 | Feldman | 568/411 |
| 4,501,645 | 2/1985 | Berg et al. | 203/60 |
| 4,544,454 | 10/1985 | Berg et al. | 203/57 |
| 5,304,684 | 4/1994 | Nishida et al. | 568/410 |
| 5,338,411 | 8/1994 | Berg | 203/60 |
| 5,437,770 | 8/1995 | Berg | 203/60 |
| 5,504,239 | 4/1996 | Nehl et al. | 568/913 |

*Primary Examiner*—Virginia Manoharan

[57] ABSTRACT

Methyl ethyl ketone cannot be separated from ethanol by distillation or rectification because of the closeness of their boiling points. Methyl ethyl ketone is readily separated from ethanol by azeotropic distillation. Effective agents are amyl acetate, methyl formate, 2,2-dimethyl butane and 2,3-dimethyl butane.

1 Claim, No Drawings

SEPARATION OF METHYL ETHYL KETONE FROM ETHANOL BY AZEOTROPIC DISTILLATION

FIELD OF THE INVENTION

This invention relates to a method for separating methyl ethyl ketone from ethanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotromic distillation agents is the chance in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Methyl ethyl ketone and ethanol boil only one degree apart and have a relative volatility of 1.1 which makes it impossible to separate them by conventional distillation or rectification. Table 2 shows that with an agent giving a relative volatility of 1.65, only 26 actual plates are required to get 99% purity.

TABLE 2

Theoretical and Actual Plates Required vs. Relative Volatility for Methyl Ethyl Ketone from Ethanol Separation

| Relative Volatility | Theoretical Plates Required At Total Reflux, 99% Purity | Actual Plates Required, 75% Efficiency |
|---|---|---|
| 1.3 | 34 | 46 |
| 1.4 | 26 | 35 |
| 1.65 | 19 | 26 |

OBJECTIVE OF THE INVENTION

The object of this invention is to provide a process or method of azeotropic distillation that will enhance the relative volatility of methyl ethyl ketone from ethanol in their separation in a rectification column. It is a further object of this invention to identify effective azeotropic distillation agents that are stable and can be recycled.

SUMMARY OF THE INVENTION

The objects of this invention are provided by a process for the separation of methyl ethyl ketone from ethanol which entails the use of certain organic compounds when employed as the agent in azeotropic distillation.

TABLE 3

Rffective Azeotropic Distillation Agents For Separating Methyl Ethyl Ketone From Ethanol

| Compounds | Relative Volatility |
|---|---|
| None | 1.06 |
| Amyl acetate | 1.4 |
| Methyl formate | 1.3 |
| 2,2-Dimethyl butane | 1.65 |
| 2,3-Dimethyl butane | 1.4 |

DETAILED DESCRIPTION OF THE INVENTION

I have discovered that certain organic compounds will effectively increase the relative volatility between methyl ethyl ketone an ethanol during rectification when employed as the agent in azeotropic distillation. They are amyl acetate, methyl formate, 2,2-Dimethyl butane and 2,3-Dimethyl butane.

WORKING EXAMPLE

1. Fifty grams of methyl ethyl ketone-ethanol and fifty grams of 2,2-dimethyl butane were charged to a vapor-liquid equilibrium still and refluxed for two hours. The vapor composition was 71.7% methyl ethyl ketoneand- 28.3% ethanol. The liquid composition was 60.5% methyl ethyl ketone and 39.5% ethanol. This is a relative volatility of 1.65.

THE USEFULNESS OF THE INVENTION

The usefulness of this invention can be demonstrated by referring to the data presented in Tables 1, 2 and 3 . All of the successful agents show that methyl ethyl ketone can be separated from ethanol by means of azeotropic distillation in a rectification column and that the ease of separation as measured by relative volatility is considerable.

I claim:

1. A method for recovering methyl ethyl ketone from a mixture of methyl ethyl ketone and ethanol which consists essentially of distilling a mixture of methyl ethyl ketone and ethanol in the presence of an azeotrope forming agent, recovering the methyl ethyl ketone and the azeotrope forming agent as overhead product and obtaining the ethanol as bottoms product, wherein said azeotrope forming agent consists of one material selected from the group consisting of amyl acetate, methyl formate, 2,2-dimethyl butane and 2,3-dimethyl butane.

* * * * *